US009322771B2

United States Patent
Son et al.

(10) Patent No.: US 9,322,771 B2
(45) Date of Patent: Apr. 26, 2016

(54) APPARATUS AND METHOD FOR MONITORING SEMICONDUCTOR FABRICATION PROCESSES USING POLARIZED LIGHT

(71) Applicant: Samsung Electronics Co., Ltd., Suwon-si (KR)

(72) Inventors: Woong-Kyu Son, Hwaseong-si (KR); Kwang-Hoon Kim, Yongin-si (KR); Deok-Yong Kim, Gunpo-si (KR); Sung-Soo Moon, Seoul (KR); Jung-Hoon Byun, Hwaseong-si (KR); Ji-Hye Lee, Suwon-si (KR); Choon-Shik Leem, Seoul (KR); Soo-Bok Chin, Seoul (KR)

(73) Assignee: Samsung Electronics Co., Ltd. (KR)

( * ) Notice: Subject to any disclaimer, the term of this patent is extended or adjusted under 35 U.S.C. 154(b) by 153 days.

(21) Appl. No.: 14/197,608

(22) Filed: Mar. 5, 2014

(65) Prior Publication Data
US 2014/0264052 A1 Sep. 18, 2014

(30) Foreign Application Priority Data

Mar. 8, 2013 (KR) ........................ 10-2013-0025283

(51) Int. Cl.
*G01N 21/33* (2006.01)
*G01N 21/21* (2006.01)
*G03F 7/22* (2006.01)
*G03F 7/20* (2006.01)

(52) U.S. Cl.
CPC ................. *G01N 21/33* (2013.01); *G01N 21/21* (2013.01); *G03F 7/70625* (2013.01)

(58) Field of Classification Search
CPC ...................................................... G01N 21/33
See application file for complete search history.

(56) References Cited

U.S. PATENT DOCUMENTS

| 5,013,141 | A | * | 5/1991 | Sakata | ................. G02B 5/1828 349/201 |
| 6,529,276 | B1 | * | 3/2003 | Myrick | ..................... G01J 3/02 356/310 |
| 7,006,224 | B2 | | 2/2006 | Some | |
| 7,488,688 | B2 | * | 2/2009 | Chung | .............. H01L 21/02057 216/67 |
| 7,643,137 | B2 | | 1/2010 | Sugihara et al. | |
| 7,968,844 | B2 | | 6/2011 | Kim | |
| 2002/0048019 | A1 | * | 4/2002 | Sui | .......................... G01N 21/21 356/369 |
| 2010/0202055 | A1 | * | 8/2010 | Norton | ...................... G01J 3/02 359/568 |

(Continued)

FOREIGN PATENT DOCUMENTS

| JP | 07-022483 | 1/1995 |
| JP | 11-271233 | 10/1999 |

(Continued)

*Primary Examiner* — David Porta
*Assistant Examiner* — Jeremy S Valentiner
(74) *Attorney, Agent, or Firm* — Myers Bigel & Sibley

(57) ABSTRACT

The inventive concept provides apparatuses and methods for monitoring semiconductor fabrication processes in real time using polarized light. In some embodiments, the apparatus comprises a light source configured to generate light, a beam splitter configured to reflect the light toward the wafer being processed, an objective polarizer configured to polarize the light reflected toward the wafer and to allow light reflected by the wafer to pass therethrough, a blaze grating configured to separate light reflected by the wafer according to wavelength, an array detector configured to detect the separated light and an analyzer to analyze the three-dimensional profile of the structure/pattern being formed in the wafer.

18 Claims, 7 Drawing Sheets

(56) References Cited

U.S. PATENT DOCUMENTS

2010/0284027 A1 11/2010 Scheiner
2011/0035189 A1 2/2011 Fujii
2013/0321810 A1* 12/2013 Wang .................. G03F 7/70625
356/369

FOREIGN PATENT DOCUMENTS

| JP | 2003-068814 | 3/2003 |
| KR | 10-1999-0080533 A | 11/1999 |
| KR | 10-2011-0112725 A | 10/2011 |

* cited by examiner

APPARATUS AND METHOD FOR MONITORING SEMICONDUCTOR FABRICATION PROCESSES USING POLARIZED LIGHT

CROSS-REFERENCE TO RELATED APPLICATION

This application claims priority under 35 U.S.C. §119 to Korean Patent Application No. 10-2013-0025283, filed Mar. 8, 2013 in the Korean Intellectual Property Office, the disclosure of which is hereby incorporated by reference in its entirety.

FIELD OF THE INVENTION

The inventive concept relate to apparatuses and methods for monitoring semiconductor fabrication processes.

BACKGROUND

As the integration density of semiconductor devices has increased, the patterns formed in such devices have become increasingly fine, dense and deep. Conventional methods of analyzing semiconductor structures and patterns (e.g., methods using a scanning electron microscope or a transmission electron microscope) are destructive and result in significant temporal and monetary losses. There is thus a need for improved methods of monitoring/analyzing structures and patterns formed in semiconductor devices.

SUMMARY

Exemplary embodiments of the inventive concept provide apparatuses for monitoring a semiconductor fabrication process. In some embodiments, the apparatus is configured to monitor the process in real time (e.g., as a pattern is being etched into a wafer). In some embodiments, the apparatus comprises a polarizing spectroscopic reflector module comprising a light source configured to generate light (e.g., polychromatic ultraviolet light), a selective reflector (e.g., a beam splitter) configured to reflect light generated by the light source toward a workpiece (e.g., a wafer), a light polarizer (e.g., an objective polarizer) configured to polarize light reflected toward the workpiece by the selective reflector and to allow light reflected by the workpiece to pass therethrough, a blaze grating configured to separate light reflected by the workpiece according to wavelength, and an array detector configured to detect separated light reflected by the blaze grating. The apparatus may further comprise a chamber, and the polarizing spectroscopic reflector module may be at least partially disposed in the chamber. The apparatus may further comprise a gas distributor configured to mix two or more reaction gases and to introduce the mixed reaction gases into the interior of the chamber. The apparatus may further comprise a susceptor configured to receive the workpiece. The polarizing spectroscopic reflector module may further comprise an analyzer configured to analyze light detected by the array detector. The polarizing spectroscopic reflector module may further comprise a reflecting aperture configured to reflect a portion of the light reflected by the workpiece and passed through the light polarizer. The polarizing spectroscopic reflector module may further comprise a camera configured to sense light reflected by the reflecting aperture. The polarizing spectroscopic reflector module may further comprise a display unit configured to display one or more images (e.g., virtual images of a structures formed in a wafer), three-dimensional ("3D") representations (e.g., 3D representations of a structures formed in a wafer) and/or graphical representations (e.g., graphical representations of the intensity of light reflected by the workpiece as a function of wavelength).

Exemplary embodiments of the inventive concept provide apparatuses for inspecting a workpiece (e.g., a wafer) using polarized light. In some embodiments, the apparatus is configured to inspect the workpiece in real time (e.g., as a pattern is being etched into the workpiece). In some embodiments, the apparatus comprises a chamber and a polarizing spectroscopic reflector module configured to radiate polarized light onto a workpiece and to sense light reflected by the workpiece. In some such embodiments, the polarizing spectroscopic reflector module comprises a light source configured to generate light (e.g., polychromatic ultraviolet light), a selective reflector (e.g., a beam splitter) configured to reflect light generated by the light source toward the workpiece, a light polarizer (e.g., an objective polarizer) configured to polarize light reflected toward the workpiece by the selective reflector and to allow light reflected by the workpiece to pass therethrough, a blaze grating configured to separate light that has been reflected by the workpiece according to wavelength, and an array detector configured to detect separated light reflected by the blaze grating. The apparatus may further comprise a gas distributor configured to mix two or more reaction gases and to introduce the mixed reaction gases into the chamber. The apparatus may further comprise a susceptor configured to receive the workpiece. The polarizing spectroscopic reflector module may further comprise an analyzer configured to analyze light detected by the array detector. The polarizing spectroscopic reflector module may further comprise a reflecting aperture configured to reflect a portion of the light reflected by the workpiece and passed through the light polarizer. The polarizing spectroscopic reflector module may further comprise a camera configured to sense light reflected by the reflecting aperture. The polarizing spectroscopic reflector module may further comprise a display unit configured to display one or more images (e.g., virtual images of a structures formed in a wafer), 3D representations (e.g., 3D representations of a structures formed in a wafer) and/or graphical representations (e.g., graphical representations of the intensity of light reflected by the workpiece as a function of wavelength).

Exemplary embodiments of the inventive concept provide apparatuses for inspecting a workpiece using polarized light. In some embodiments, the apparatus includes a chamber having a susceptor configured to place a workpiece in a lower portion of an inside thereof; and a polarizing spectroscopic reflector module disposed in a top of the chamber. In some embodiments, the polarizing spectroscopic reflector module includes a light source configured to generate light; a beam splitter configured to receive the light generated from the light source and reflect a portion of the received light; an objective polarizer configured to polarize the portion of the light reflected by the beam splitter and radiate the polarized light to the workpiece on the susceptor; a reflecting aperture configured to partially pass the reflected polarized light passing through the beam splitter; a blaze grating configured to reflect the reflected polarized light partially passing through the reflecting aperture; and an array detector configured to sense the reflected polarized light divided and reflected by the blaze grating. In some embodiments, reflected polarized light reflected from the workpiece reversely passes through the objective polarizer and the reflected polarized light reversely passed through the objective polarizer partially passes through the beam splitter. In some embodiments, an optical axis of the polarized light radiated to a surface of the susceptor from the objective polarizer is perpendicular to the surface of the susceptor. In some embodiments, the polarizing spectroscopic reflector module is disposed in a center of a top of the chamber. In some embodiments, the chamber further includes a gas distributor disposed in the upper portion of the inside thereof. In some embodiments, the gas distributor includes a space configured to mix reaction gases, and a baffle plate configured to supply the reaction gases to the inside of the chamber. In some embodiments, the polarizing spectroscopic reflector module vertically passes through a central portion of the baffle plate. In some embodiments, the beam splitter and the reflecting aperture reflect a portion of the received light and pass another portion of the received light.

Exemplary embodiments of the inventive concept provide methods of monitoring a semiconductor fabrication process. In some embodiments, the process is monitored in real time (e.g., as a pattern is being etched into a wafer). In some embodiments, the method comprises radiating polarized light (e.g., a first polarized light, a second polarized light, a third polarized light, etc.) onto a workpiece and analyzing light reflected by the workpiece. In some such embodiments, the first polarized light is polarized to a first direction and the second polarized light is polarized to a second direction different from the first direction (e.g., a second direction perpendicular to the first direction). The polarized light radiated onto the workpiece may comprise polychromatic ultraviolet light. Analyzing light reflected by the workpiece may comprise separating light reflected by the workpiece according to wavelength. Analyzing light reflected by the workpiece may comprise comparing two or more spectrums of light reflected by the workpiece (e.g., a first spectrum comprising light that oscillates in a first direction, a second spectrum comprising light that oscillates in a second direction, a third spectrum comprising light that oscillates in a third direction, etc.). Each spectrum of light reflected by the workpiece may comprise a plurality of intensities divided according to the wavelength of light reflected.

Exemplary embodiments of the inventive concept provide methods of inspecting a workpiece (e.g., a wafer) using polarized light. In some embodiments, the workpiece is inspected in real time (e.g., as a pattern is being etched into the workpiece). In some embodiments, the method comprises radiating polarized light (e.g., a first polarized light, a second polarized light, a third polarized light, etc.) onto a workpiece and analyzing polarized light reflected from the workpiece. Polarized light radiated onto the workpiece may comprise polychromatic ultraviolet light. Analyzing light reflected by the workpiece may comprise diving light reflected by the workpiece according to wavelength. Analyzing light reflected by the workpiece may comprise comparing two or more spectrums of light reflected by the workpiece (e.g., a first spectrum comprising light that oscillates in a first direction, a second spectrum comprising light that oscillates in a second direction, a third spectrum comprising light that oscillates in a third direction, etc.). Each spectrum of light reflected by the workpiece may comprise a plurality of intensities divided according to the wavelength of light reflected.

Exemplary embodiments of the inventive concept provide methods of generating a 3D (3D) profile of a structure (e.g., a via hole) or pattern in workpiece. In some embodiments, the method comprises comparing two or more asymmetries (e.g., a first asymmetry calculated during a first cycle of a monitoring process and a second asymmetry calculated during a second cycle of the monitoring process). The monitoring process may comprise radiating polarized light (e.g., a first polarized light, a second polarized light, a third polarized light, etc.) onto a workpiece and analyzing light reflected by the workpiece. Asymmetries may be calculated by comparing two or more spectrums of light reflected by the workpiece (e.g., a first spectrum comprising light that oscillates in a first direction, a second spectrum comprising light that oscillates in a second direction, a third spectrum comprising light that oscillates in a third direction, etc.). Spectrums of light reflected by the workpiece may comprise a plurality of intensities divided according to the wavelength of light reflected.

BRIEF DESCRIPTION OF THE DRAWINGS

The foregoing and other aspects, features and advantages of the inventive concept will be apparent from the following detailed description of exemplary embodiments of the inventive concept, as illustrated in the accompanying drawings, in which like reference characters refer to the same parts throughout the different views. The drawings are not necessarily to scale, emphasis instead being placed upon illustrating the principles of the inventive concept. In the drawings:

FIG. 5A depicts an intensity spectrum of light polarized in a first direction; FIG. 5B depicts an intensity spectrum of light polarized in a second direction different from the first direction; FIG. 5C is a composite graph depicting the intensity spectrum of light polarized in the first direction (solid line) and the intensity spectrum of light polarized in the second direction (dashed line)

DETAILED DESCRIPTION

Figure 1:
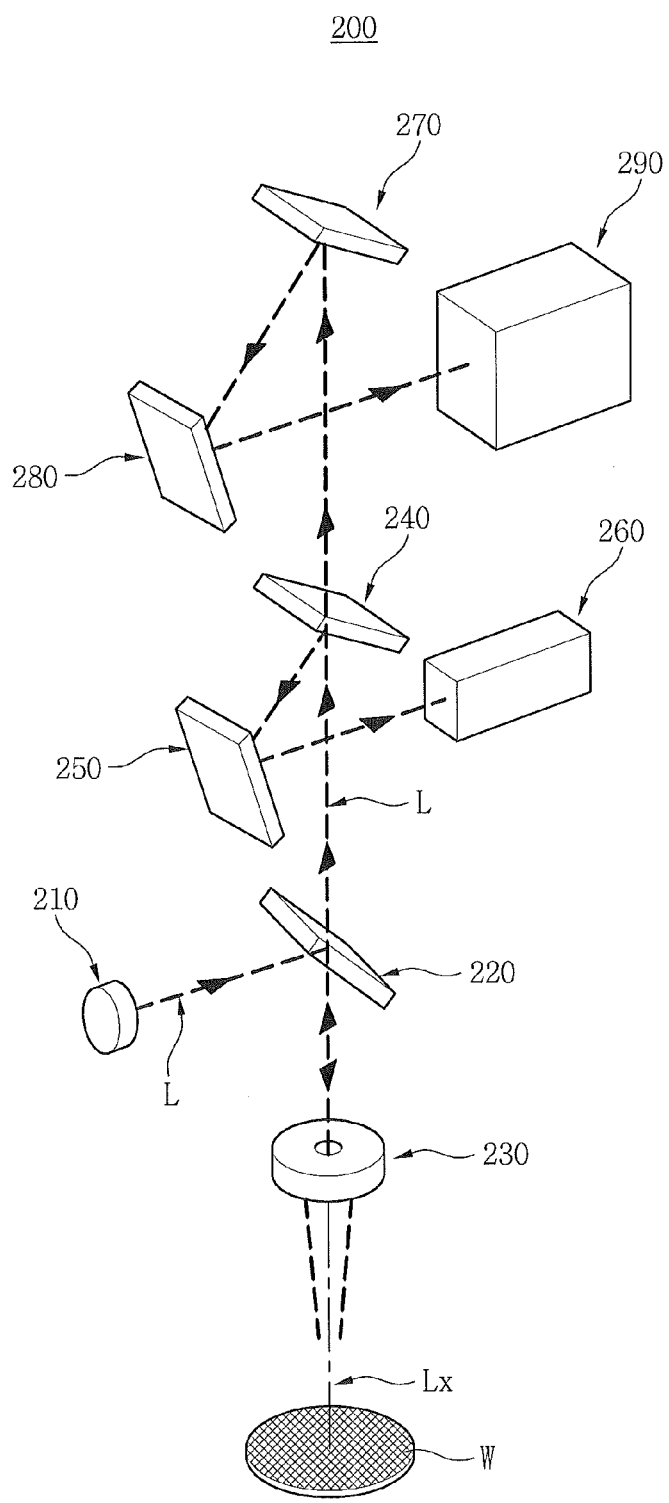
FIG. 1 is a schematic illustration of a polarizing spectroscopic reflector module according to exemplary embodiments of the inventive concept.

The inventive concept will now be described more fully hereinafter with reference to the accompanying drawings, in which exemplary embodiments of the invention are shown. This inventive concept may, however, be embodied in different forms and should not be construed as limited to the exemplary embodiments set forth herein. Rather, these embodiments are provided so that this disclosure will be thorough and complete, and will fully convey the scope of the inventive concept to those skilled in the art.

Exemplary embodiments of the inventive concepts are described herein with reference to perspective view illustrations, plan view illustrations and/or cross-sectional illustrations that are schematic illustrations of idealized embodiments (and intermediate structures) of exemplary embodiments. As such, variations from the shapes of the illustrations as a result, for example, of manufacturing techniques and/or tolerances, are to be expected. Thus, exemplary embodiments of the inventive concepts should not be construed as limited to the particular shapes of regions illustrated herein, but are to include deviations in shapes that result, for example, from manufacturing. For example, an etched region illustrated as a rectangle may, in some embodiments, have rounded or curved features having a predetermined curvature. Thus, the regions illustrated in the drawings are schematic in nature and their shapes are not intended to limit the scope of the inventive concept.

In the drawings, the sizes and relative sizes of respective elements, components, layers, regions and sections may be exaggerated for clarity. Like numerals refer to like elements throughout. Names and functions of components not shown or not labeled with reference numerals will easily be understood from the drawings and descriptions contained herein.

The terminology used herein is for the purpose of describing exemplary embodiments of the inventive concept and is not intended to be limiting of the inventive concept.

Unless otherwise defined, all terms used herein (including technical and scientific terms) have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present.

It will be understood that when an element or layer is referred to as being "adjacent to" another element or layer, it can be directly adjacent to the other element or layer or intervening elements or layers may be present. In contrast, when an element is referred to as being "directly adjacent to" another element or layer, there are no intervening elements or layers present.

It will be understood that when an element or layer is referred to as being "adjacent to" another element or layer, one or more portions of the two elements/layers may overlap unless otherwise indicated herein or clearly contradicted by context.

It will be understood that, although the terms "first," "second," "third," etc. may be used herein to describe various elements, components, regions, layers and/or sections, such elements, components, regions, layers and/or sections are not limited by those terms. Unless the context clearly indicates otherwise indicated, the terms are used only to distinguish one element, component, region, layer or section from another element, component, region, layer or section. Thus, a first element, component, region, layer or section discussed below could be termed a second element, component, region, layer or section without departing from the teachings of the inventive concept.

Spatially relative terms, such as "beneath," "below," "lower," "above," "upper" and the like, may be used herein for ease of description to describe one element or feature's relationship to another element(s) or feature(s) as illustrated in the drawings. It will be understood that the spatially relative terms are intended to encompass different orientations of the device in use or operation in addition to the orientation depicted in the drawings. For example, if the device in the drawings is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

As used herein, the terms "a," "an," "the" and similar referents, when used in the context of describing the inventive concept (especially in the context of the following claims), are to be construed to cover both the singular and the plural forms, unless otherwise indicated herein or clearly contradicted by context.

As used herein, the terms "comprise," "comprising," "have," "having," "include," "including," "contain," "containing" and grammatical variants thereof specify the presence of stated features, integers, steps, operations, elements, components, regions, layers and/or sections, but do not preclude the presence or addition of one or more other features, integers, steps, operations, elements, components, regions, layers, sections and/or groups thereof.

As used herein, the term "and/or" refers to and encompasses any and all possible combinations of one or more of the associated listed items.

As used herein, the term "about," when referring to a measurable value such as an amount of a compound, time, temperature, and the like, is meant to encompass variations of 20%, 10%, 5%, 1%, 0.5%, or even 0.1% of the specified amount.

As used herein, the term "substantially vertical" means that the longitudinal axis of the referenced item (e.g., an aperture sidewall) is substantially aligned with the vertical axis of the substrate upon which the referenced item is formed. In some embodiments, a referenced item is deemed to be substantially vertical if the orientation of its longitudinal axis differs from the vertical axis of the substrate by no more than about 0.1°, 0.25°, 0.5°, 1°, 1.5°, 2°, 2.5°, 3°, 4°, 5°. In some embodiments, a referenced item is deemed to be substantially vertical if the orientation of its longitudinal axis differs from the vertical axis of the substrate by about 0.1°, 0.25°, 0.5°, 1°, 1.5°, 2°, 2.5°, 3°, 4°, 5°. In some embodiments, a referenced item is deemed to be substantially vertical if the orientation of its longitudinal axis differs from the vertical axis of the substrate by less than 0.1°, 0.25°, 0.5°, 1°, 1.5°, 2°, 2.5°, 3°, 4° or 5°.

Hereinafter, exemplary embodiments of the inventive concept will be explained with reference to the accompanying drawings Apparatuses according to exemplary embodiments of the inventive concept will be described with respect to FIGS. 1-3.

Apparatuses of the inventive concept may be configured for use with any suitable semiconductor fabrication process, including, but not limited to, etching processes, deposition processes, growth processes, cleaning processes, ion implantation processes and planarization processes. For example, in some embodiments, the apparatus is configured to monitor and/or inspect the 3D profile(s) of a structure/pattern during an etching process.

As shown in FIG. 1, in some embodiments, the inventive concept provides a polarizing spectroscopic reflector module 200 comprising a light source 210, a light polarizer 230 configured to polarize light generated by the light source 210 before it reaches a workpiece W and an array detector 290 configured to sense light reflected by the workpiece W.

Apparatuses of the inventive concept may comprise any suitable light source. In some embodiments, the light source generates polychromatic ultraviolet light.

Apparatuses of the inventive concept may comprise any suitable light polarizer, including, but not limited to, objective polarizers. In some embodiments, the light polarizer comprises, consists essentially of or consists of an objective polarizer.

Light polarizers of the inventive concept may be configured to polarize light in any suitable direction/azimuth. In some embodiments, the light polarizer is configured to polarize light generated by the light source 210 such that it oscillates in a one-dimensional direction. In some embodiments, the light polarizer is configured to selectively and sequentially polarize light generated by the light source 210 to one of a plurality of directions/azimuths (e.g., a first direction, a second direction different than the first direction, a third direction different than the first and second directions, etc.), Such variation may be achieved by selectively rotating the light polarizer around an optical axis Lx.

Light reflected by the workpiece W may comprise information related to one or more structures/patterns formed in the workpiece W. For example, polarized light reflected by the workpiece W may comprise information related to a 3D structure/pattern in the workpiece W.

Apparatuses of the inventive concept may comprise any suitable array detector, including, but not limited to, photodiode array detectors.

Array detectors of the inventive concept may be configured to detect light having any suitable wavelength, including, but not limited to, light having a wavelength in the range of about 100 nm to about 400 nm, light having a wavelength in the range of about 315 nm to about 400 nm, light having a wavelength in the range of about 280 nm to about 315 nm and light having a wavelength in the range of about 100 nm to about 280 nm.

Array detectors of the inventive concept may be configured to detect light polarized in any suitable direction/azimuth, including, but not limited to, light polarized in a one-dimensional direction perpendicular to a surface (e.g., the upper surface) of the workpiece W.

Array detectors of the inventive concept may be configured to perform any suitable analysis, including, but not limited to, analysis of the intensity, wavelength and/or polarity of light reflected from a workpiece.

Array detectors of the inventive concept may be configured to generate any suitable type of data, including, but not limited to, data associated with one or more characteristics of light reflected from a workpiece (e.g., data associated with the intensity, wavelength and/or polarity of light reflected from a workpiece). In some embodiments, the array detector is configured to generate graphical representations (e.g., intensity spectrums representing light reflected by the workpiece), images (e.g., virtual images of the upper surface of the workpiece and/or of a structure/pattern in/on the workpiece) and 3D representations (e.g., 3D representations of structures/patterns in/on the workpiece). In some embodiments, the array detector is configured to forward data associated with one or more the characteristics of light reflected from a workpiece to an analyzer that is itself configured to generate graphical representations (e.g., intensity spectrums representing light reflected by a workpiece), images (e.g., virtual images of the upper surface of a workpiece and/or of a structure/pattern in/on a workpiece) and/or 3D representations (e.g., 3D representations of structures/patterns in/on a workpiece).

As shown in FIG. 1, polarizing spectroscopic reflector modules of the inventive concept may comprise a first reflector 220 configured to reflect light generated by the light source 210 toward the workpiece W. In such embodiments, the first reflector 220 may be configured to reflect light generated by the light source 210 through the light polarizer 230.

Thus, as shown in FIG. 1, in some embodiments of the inventive concept, the polarizing spectroscopic reflector modules comprises first reflector 220 configured to reflect light generated by the light source 210 through the light polarizer 230 and toward the workpiece W.

Apparatuses of the inventive concept may comprise any suitable first reflector. In some embodiments, the first reflector comprises, consists essentially of or consists of a selective reflector (e.g., a beam splitter) configured to reflect some light and to allow other light to pass therethrough. For example, the first reflector may comprise, consist essentially of or consist of a selective reflector configured to reflect at least a portion of the light generated by a light source and to allow at least a portion of the light reflected from a workpiece to pass therethrough.

As shown in FIG. 1, polarizing spectroscopic reflector modules of the inventive concept may comprise a light separator 270 configured to disperse and/or diffract light reflected by the workpiece W according to wavelength. In such embodiments, light reflected by the workpiece W may be reflected toward the array detector 290 by the light separator 270.

Apparatuses of the inventive concept may comprise any suitable light separator. In some embodiments, the light separator comprises, consists essentially of or consists of a blaze grating configured to disperse and/or diffract polarized light to various angles according to the wavelengths of the polarized light.

Figure 2:
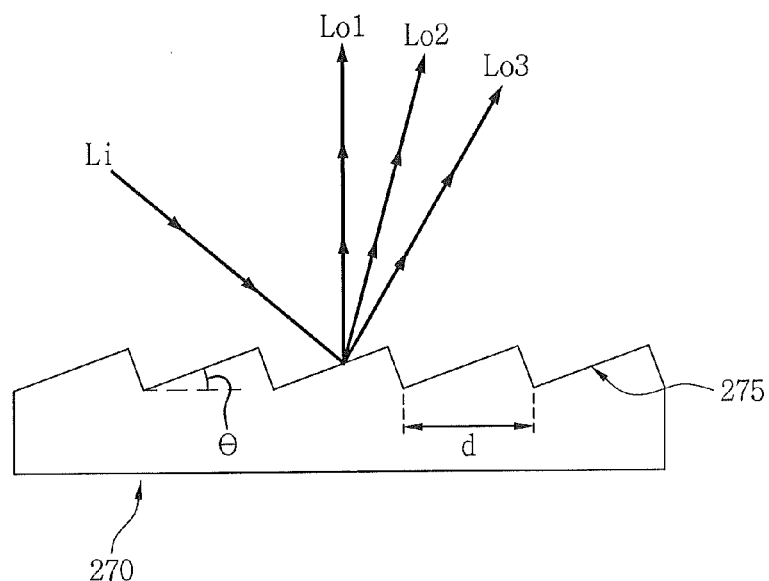
FIG. 2 is a cross-sectional schematic illustration of a blaze grating of according to exemplary embodiments of the inventive concept.

As shown in FIG. 2, light separators of the inventive concept may comprise, consist essentially of or consist of a blaze grating 270 having a plurality of reflecting surfaces 275 inclined in a sawtooth or washboard form in a cross-sectional view. Each of the reflecting surfaces 275 may have an arbitrary angle $\theta$ and an arbitrary width d. Light incident to the reflecting surfaces 275 may be reflected and diffracted to various exit angles according to the angle $\theta$ and the width d of the reflecting surface and the wavelength of the light reflected. For example, as shown in FIG. 3, incident light Li may be divided (according to wavelengths) and reflected or diffracted into a plurality of exit lights Lo1, Lo2, and Lo3.

As shown in FIG. 1, polarizing spectroscopic reflector modules of the inventive concept may comprise a camera 260 configured to detect light reflected by the workpiece W.

Apparatuses of the inventive concept may comprise any suitable camera. In some embodiments, the camera is operatively connected to an analyzer and/or a display unit. In some embodiments, the camera is configured to selectively detect light of a specific wavelength or range of wavelengths (e.g., light having a wavelength in the range of about 100 nm to about 400 nm, about 315 nm to about 400 nm, about 280 nm to about 315 nm, about 100 nm to about 280 nm, etc.).

As shown in FIG. 1, polarizing spectroscopic reflector modules of the inventive concept may comprise a reflecting aperture 240 configured to reflect light reflected by the workpiece W. In such embodiments, light reflected by the workpiece W may be reflected toward a camera 260 by the reflecting aperture 240.

Apparatuses of the inventive concept may comprise any suitable reflecting aperture. In some embodiments, the reflecting aperture comprises, consists essentially of or consists of a selective reflector (e.g., a beam splitter).

As shown in FIG. 1, polarizing spectroscopic reflector modules of the inventive concept may comprise one or more mirrors. For example, in some embodiments, the polarizing spectroscopic reflector module comprises an array mirror 280 configured to reflect light toward the array detector 290. Similarly, in some embodiments, the polarizing spectroscopic reflector module comprises an image mirror 250 configured to reflect light toward a camera 260.

As shown in FIG. 1, polarizing spectroscopic reflector modules of the inventive concept may be configured such that a portion of the light reflected by a workpiece W is reflected toward and sensed by a camera 260 and another portion of the light reflected by a workpiece W is reflected toward and sensed by an array detector 290.

Apparatuses of the inventive concept may comprise any suitable mirror. In some embodiments, one or more of the mirrors comprises, consists essentially of or consists of a plane mirror.

Accordingly, as shown in FIG. 1, in some exemplary embodiments, the polarizing spectroscopic reflector module 200 comprises a light source 210, a first reflector 220 (e.g., a beam splitter), a light polarizer 230 (e.g., an objective polarizer), a reflecting aperture 240, an image mirror 250, a camera 260, a light separator 270 (e.g., a blaze grating), an array mirror 280 and an array detector 290. The light source 210 is configured to generate light L of various wavelengths (e.g., polychromatic ultraviolet light) and to radiate the light L to the first reflector 220. The first reflector 220 is configured to reflect at least a portion of the light received from the light source 210 to the light polarizer 230. The light polarizer 230 is configured to polarize light received from the first reflector 220 such that it oscillates in a plurality of one-dimensional directions (e.g., to a first one-dimensional direction, to a second one-dimensional direction, to a third one-dimensional direction, etc.) as it passes through to the workpiece W (e.g., to the upper surface of the workpiece W). Polarized light reflected by the workpiece W comprises structure/pattern information (e.g., information regarding the 3D shape of a via hole V formed in the workpiece W). Polarized light reflected by the workpiece W (e.g., light reflected by the upper surface of the workpiece W) passes through the light polarizer 230 to the first reflector 220. The first reflector 220 is configured to allow at least a portion of the polarized light reflected by the workpiece W to pass through to the reflecting aperture 240. The reflecting aperture 240 is configured to allow a portion of the polarized light reflected by the workpiece W to pass through to the light separator 270 and to further reflect a portion of the polarized light reflected by the workpiece W toward the image mirror 250, which is itself configured to further reflect the polarized light reflected by the reflecting aperture 240 toward the camera 260. The camera 260 is configured to detect at least a portion of the polarized light reflected by the image mirror 250. Light detected by the camera 260 may be directly displayed on a display unit 400 or may be processed by an analyzer 300 and then displayed on a display unit 400. Light detected by the camera 260 may be displayed visually and/or virtually. The light separator 270 is configured to further reflect the polarized light reflected by the workpiece W toward the array mirror 280, which is itself configured to further reflect the polarized light reflected by the light separator 270 toward the array detector 290. The array detector 290 is configured to detect and analyze at least a portion of the polarized light reflected by the array mirror 280.

As will be understood by those skilled in the art, one or more of the aforementioned components may be omitted from the polarizing spectroscopic reflector module without materially departing from the inventive concept. For example, in some embodiments, the reflecting aperture, the image mirror and the camera are omitted. In other embodiments, the image mirror is omitted, and light is reflected directly from the reflecting aperture to the camera. Similarly, in some embodiments, the array mirror is omitted, and light is reflected directly from the light separator to the array detector.

Figure 3:
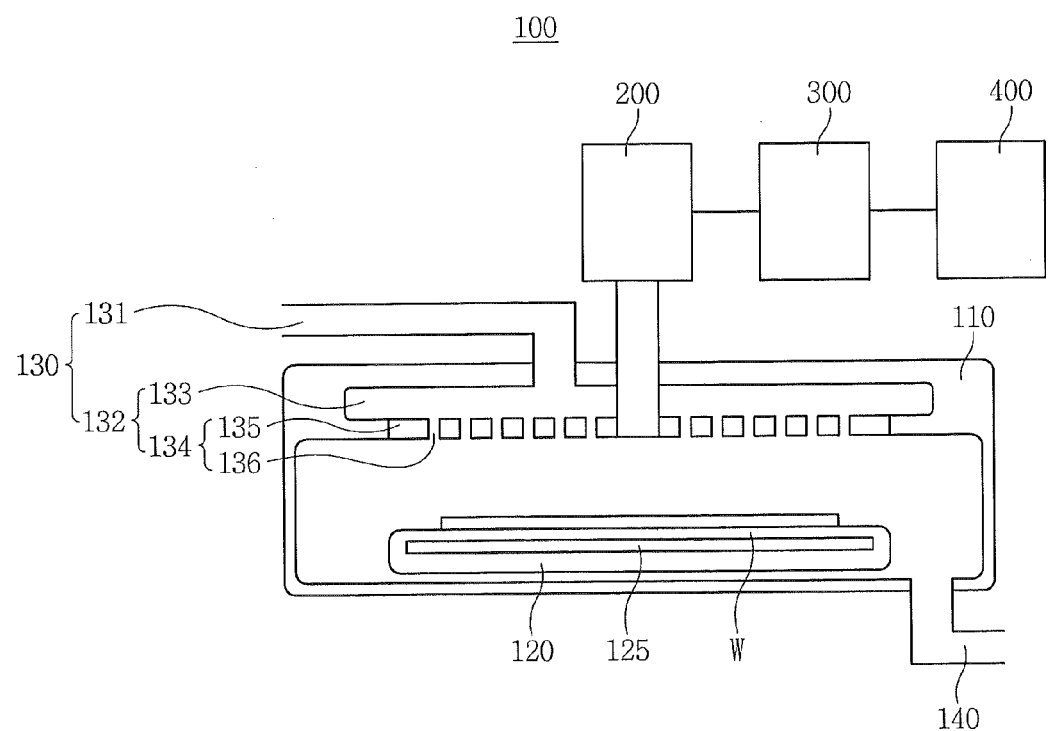
FIG. 3 is a schematic illustration of an apparatus according to exemplary embodiments of the inventive concept.

As shown in FIG. 3, in some embodiments, the inventive concept provides an apparatus 100 comprising a chamber 110 and a polarizing spectroscopic reflector module 200. The polarizing spectroscopic reflector module 200 may be partially or entirely disposed within the interior of the chamber 110 (e.g., partially disposed in the upper portion of the chamber, as shown in FIG. 3).

Apparatuses of the inventive concept may comprise any suitable chamber. In some embodiments, the chamber comprises, consists essentially of or consists of a susceptor, a temperature controller, a gas supplying unit and a gas exhausting port. The chamber may provide an airtight space in which one or more semiconductor fabrication processes (e.g., etching processes, deposition processes, growth processes, cleaning processes, ion implantation processes and/or planarization processes) may be performed. In some embodiments, the chamber is vacuumized.

Apparatuses of the inventive concept may comprise any suitable susceptor. In some embodiments the susceptor is configured to receive and/or secure a workpiece (e.g., a wafer). The susceptor may be configured such that the upper surface of the workpiece is level (or substantially level) with the upper surface of the susceptor. In some embodiments, the susceptor comprises a temperature controller.

Apparatuses of the inventive concept may comprise any suitable temperature controller. In some embodiments, the temperature controller comprises, consists essentially of or consists of a heater (e.g., a heating coil) and/or a cooler (e.g., a unit that circulates water or a refrigerant). The temperature controller may be operatively connected to (e.g., embedded in) the susceptor and may be configured to maintain the temperature of the susceptor at or near a target temperature.

Apparatuses of the inventive concept may comprise any suitable gas supplying unit. The gas supplying unit may be configured to supply any suitable gas (or combination of gases) to the interior of the chamber, including, but not limited to, one or more etching gases and/or one or more depositing gases. In some embodiments, the gas supplying unit is configured to introduce two or more reaction gases into the interior of the chamber. In some embodiments, the gas supplying unit is configured to mix the reaction gases prior to, concurrently with or subsequent to introducing them into the interior of the chamber. In some embodiments, the gas supplying unit comprises, consists essentially of or consists of a gas supplying tube and a gas distributor. Gases supplied through the gas supplying tube may be uniformly introduced into the interior of the chamber through the gas distributor. The gas distributor may comprise, consist essentially of or consist of a gas mixer and a distribution head. The gas mixer may comprise, consist essentially of or consist of a space in which the gases supplied through the gas supplying tube are mixed. The distribution head may comprise, consist essentially of or consist a baffle plate comprising a plurality of holes and may uniformly supply the mixed gases into an inner space of the chamber through the holes.

Apparatuses of the inventive concept may comprise any suitable gas exhausting port.

Apparatuses of the inventive concept may comprise any suitable polarizing spectroscopic reflector module. In some embodiments, the apparatus comprises a polarizing spectroscopic reflector module of the inventive concept (e.g., a polarizing spectroscopic reflector module as described above with respect to FIGS. 1 and 2). The polarizing spectroscopic reflector module 200 may be combined with or separated from the chamber 110.

As shown in FIG. 3, apparatuses of the inventive concept may comprise an analyzer 300. In such embodiments, the analyzer 300 may be operatively connected to the polarizing spectroscopic reflector module 200 via any suitable connection. For example, the analyzer 300 may be directly connected to the polarizing spectroscopic reflector module 200 via a wired/wireless connection.

Apparatuses of the inventive concept may comprise any suitable analyzer.

Analyzers of the inventive concept may be configured to receive any suitable type(s) of data from the polarizing spectroscopic reflector module, including, but not limited to, data associated with the processing status of a workpiece W. In some embodiments, the analyzer is configured to receive and analyze data associated with light reflected from a workpiece disposed in/on a susceptor in the lower portion of the chamber (e.g., data associated with the intensities and wavelengths of light reflected from the workpiece).

Analyzers of the inventive concept may be configured to perform any suitable type(s) of analysis (e.g., measurements, calculations, extractions, estimates, etc.). In some embodiments, the analyzer is configured to analyze data associated with the intensities and wavelengths of polarized light reflected from the workpiece and to generate intensity spectrums of polarized light reflected by a workpiece. The analyzer may be configured to identify flaws in the structures/patterns formed in/on a workpiece (e.g., distortions in a via hole formed in a wafer).

Analyzers of the inventive concept may be configured to generate any suitable type(s) of data, including, but not limited to, graphical representations (e.g., intensity spectrums representing light reflected by the workpiece), images (e.g., virtual images of the upper surface of the workpiece and/or of a structure/pattern in/on the workpiece) and 3D representations (e.g., 3D representations of structures/patterns in/on the workpiece). The analyzer may be configured to forward the data it generates to a display unit configured to generate a visual representation (e.g., an image, a graphical representation and/or a 3D representation) of one or more structures/patterns formed in/on the workpiece.

As shown in FIG. 3, apparatuses of the inventive concept may comprise a display unit 400. The display unit 400 may be operatively connected to the polarizing spectroscopic reflector module 200 and/or to an analyzer 300 via any suitable connection. For example, the display unit 400 may be directly connected to an analyzer 300 via a wired/wireless connection.

Apparatuses of the inventive concept may comprise any suitable display unit. In some embodiments, the display unit is configured to display graphical representations (e.g., intensity spectrums representing light reflected by a workpiece), images (e.g., virtual images of the upper surface of a workpiece and/or of a structure/pattern in/on the workpiece) and/or 3D representations (e.g., 3D representations of structures/patterns in/on a workpiece).

Accordingly, as shown in FIG. 3, in some exemplary embodiments, the apparatus 100 comprises a chamber 110, a polarizing spectroscopic reflector module 200, an analyzer 300 and a display unit 400, wherein the chamber 110 comprises a susceptor 120 disposed in a lower portion of the chamber 110 and configured to receive a workpiece W, a gas supplying unit 130 disposed in the upper portion of the chamber 110 and a gas exhausting port 140 disposed in the lower portion of the chamber 110. A workpiece (e.g., a wafer) W is disposed on the upper surface of the susceptor 120. The susceptor 120 comprises a temperature controller 125. The gas supplying unit 130 comprises a gas supplying tube 131 and a gas distributor 132, which comprises a gas mixer 133 and a distribution head 134 comprising a baffle plate 135 having a plurality of holes 136 therein. The polarizing spectroscopic reflector module 200 is partially disposed in an upper portion of the interior of the chamber 110. The polarizing spectroscopic reflector module 200 passes through the gas supplying unit 130 (i.e., through a central portion of the gas mixer 133 and the distribution head 134). The polarizing spectroscopic reflector module 200 is configured to radiate polarized light through the top portion of the chamber 110 and the gas supplying unit 130 onto the upper surface of the workpiece W. The polarizing spectroscopic reflector module 200 is configured to provide data associated with the processing status of the workpiece W (e.g., data associated with the intensities and/or wavelengths of light reflected by the workpiece W) to the analyzer 300 in real time while a process is performed. The analyzer 300 is configured to receive and analyze data received from the polarizing spectroscopic reflector module 200 and to generate one or more graphical representations (e.g., intensity spectrums representing light reflected by the workpiece W), images (e.g., virtual images of the workpiece W) and/or 3D representations (e.g., 3D representations of structures/patterns in/on the workpiece W). The analyzer 300 is configured to identify flaws in the workpiece W (e.g., distortions in a via hole formed in the workpiece). The analyzer 300 is configured to provide data associated with the status of the workpiece W to the display unit 400. The display unit 400 is configured to receive data associated with the status of the workpiece W from the analyzer 300 and to display graphical representations (e.g., intensity spectrums representing light reflected by the workpiece W), images (e.g., virtual images of the upper surface of the workpiece W) and/or 3D representations (e.g., 3D representations of structures in/on the workpiece W).

Methods according to exemplary embodiments of the inventive concept will be described with respect to FIGS. 4A-6B. Methods of the inventive concept may be used in conjunction with (e.g., concurrently with) any suitable semiconductor fabrication process, including, but not limited to, etching processes, deposition processes, growth processes, cleaning processes, ion implantation processes and planarization processes. For example, in some embodiments, the method may be used to monitor and/or inspect the 3D profile of a structure/pattern during an etching process.

Figure 4A:
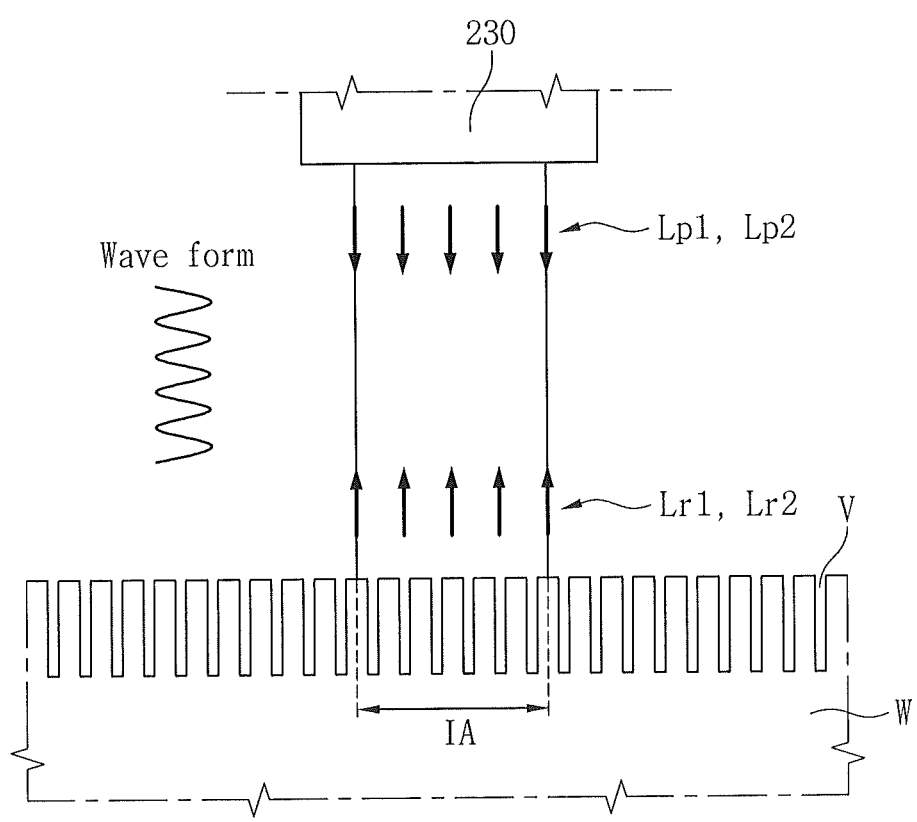
FIGS. 4A-4B are schematic illustrations of a method according to exemplary embodiments of the inventive concept.
Figure 4B:
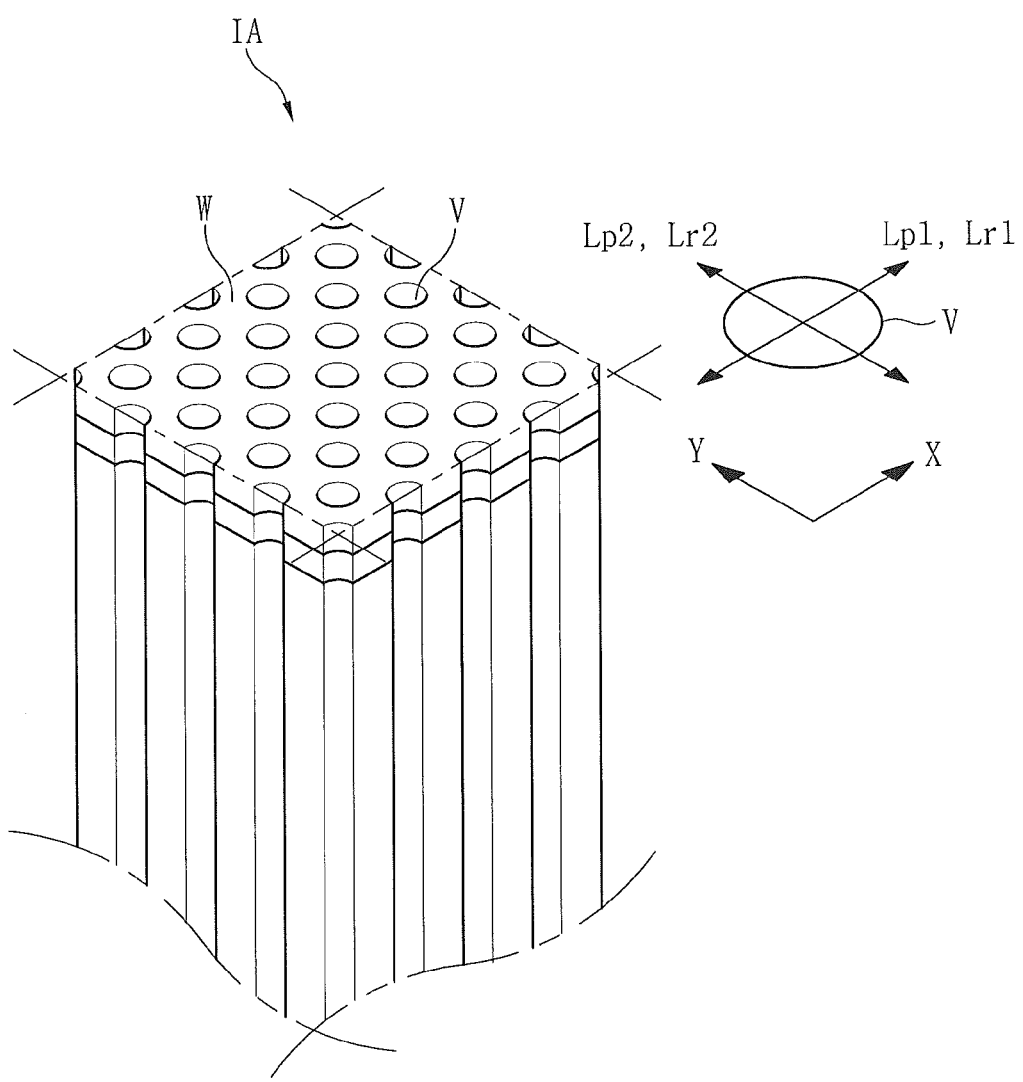

As shown in FIGS. 4A-4B, in some embodiments, the inventive concept provides a method comprising radiating a first polarized light Lp1 and a second polarized light Lp2 onto a workpiece W (e.g., a wafer) and analyzing first reflected light Lr1 and second reflected light Lr2 reflected by the workpiece W, wherein the first polarized light Lp1 is polarized in a first direction X and the second polarized light Lp2 is polarized in a second direction Y different from the first direction X. The first and second polarized lights Lp1, Lp2 may be polarized to any suitable directions. In some embodiments, the first direction X is perpendicular to the second direction Y (as shown in FIG. 5). The first and second polarized lights Lp1, Lp2 may be radiated onto one or more defined inspection areas IA, the size and/or shape of which may be arbitrarily controlled. In some embodiments, the first and second polarized lights Lp1, Lp2 are radiated onto an inspection area IA comprising a structure/pattern, such as a via hole V or a plurality of via holes.

Radiating the first polarized light Lp1 and the second polarized light Lp2 onto the workpiece W may comprise fixing a light polarizer (e.g., a light polarizer as described above with respect to FIG. 1) to a first position, radiating the first polarized light Lp1 onto the work piece W, detecting the first reflected light Lr1 reflected by the workpiece W, fixing the light polarizer to a second position, radiating the second polarized light Lp2 onto the workpiece W and detecting the second reflected light Lr2 reflected by the workpiece W. In some embodiments, the first position and the second position represent different rotational positions around an axis (e.g., an axis perpendicular to the upper surface of the workpiece W). Thus, as one skilled in the art will readily appreciate, the relationship between the oscillation direction X of the first polarized light Lp1 and the oscillation direction Y of the second polarized light Lp2 may be controlled by selectively rotating the light polarizer to different first and second positions around the axis. For example, in some embodiments, the first position is an initial position of the light polarizer and the second position is a position in which the light polarizer is rotated (e.g., by $\pi/2$, $\pi/3$, $\pi/4$, $\pi/6$ or $\pi/9$) around a rotational axis that is perpendicular to the upper surface of the workpiece W. In such embodiments, the oscillation direction X of the first polarized light Lp1 may be perpendicular to the oscillation direction Y of the second polarized light Lp2.

Methods of the inventive concept may comprise radiating additional polarized lights (e.g., a third polarized light, a fourth polarized light, a fifth polarized light, etc.) onto the workpiece. In such embodiments, each of the additional polarized lights may be polarized to a direction different from the first and second directions. Thus, in some embodiments, methods of the inventive concept may comprise radiating a first polarized light, a second polarized light and a third polarized light onto a workpiece (e.g., a wafer) and analyzing light reflected by the workpiece, wherein the first polarized light oscillates in a first direction, the second polarized light oscillates in a second direction different from the first direction and the third polarized light oscillates in a third direction different from the first direction and the second direction. The first, second and third polarized lights may oscillate in any suitable one-dimensional directions.

Any suitable polarized light may be radiated onto the workpiece, including but not limited to, polarized polychromatic ultraviolet light. Light radiated onto the workpiece may be polarized to any suitable direction/azimuth. In some embodiments, the polarized light oscillates in one or more one-dimensional directions, each of which may be perpendicular to a surface of the workpiece (e.g., the upper surface of the workpiece). In some embodiments, the light is polarized such that it oscillates in a plurality of directions/azimuths (e.g., in a first direction, in a second direction that is different than the first direction, in a third direction that is different than the first and second directions, etc.).

Light reflected by the workpiece may be analyzed in any suitable manner.

Analyzing light reflected by the workpiece may comprise separating the reflected light according to the wavelengths of the light reflected by the workpiece and analyzing at least a portion of the reflected, separated light. For example, in some embodiments, analyzing light reflected by the workpiece comprises analyzing light that has been further reflected by a light separator configured to reflect and diffract the light to various exit angles according to wavelength (see discussion above with respect to FIG. 2).

Light reflected by the workpiece may be separated according to wavelength using any suitable apparatus, including, but not limited to, apparatuses of the inventive concept. In some embodiments, light reflected by the workpiece is reflected directly to a light separator configured to disperse and/or diffract polarized light according to wavelength. For example, in some embodiments, light reflected by the workpiece is reflected directly to a blaze grating that comprises a plurality of sawtooth- or washboard-shaped reflecting surfaces configured to reflect and diffract the light to various exit angles according to the angle(s)/width(s) of the reflecting surfaces and the wavelengths of the light (see discussion above with respect to FIG. 2).

Analyzing light reflected by the workpiece may comprise comparing spectrums of light. For example, in some embodiments, analyzing light reflected by the workpiece comprises comparing a first spectrum of reflected light with a second spectrum of reflected light, wherein the first spectrum of reflected light comprises light polarized in a first direction and the second spectrum of reflected light comprises light polarized in a second direction different from the first direction. In some embodiments, each of the spectrums comprises a plurality of intensity measurements, wherein each intensity measurement (or set of intensity measurements) corresponds to light have a particular wavelength (or set of wavelengths). Thus, in some embodiments, analyzing light reflected by the workpiece comprises comparing two or more intensity spectrums (e.g., a first intensity spectrum that represents reflected light that oscillates in a first one-dimensional direction, a second intensity spectrum that represents reflected light that oscillates in a second one-dimensional direction different from the first one-dimensional direction, a third intensity spectrum that represents reflected light that oscillates in a third one-dimensional direction different from the first and second one-dimensional directions, etc.).

Light reflected by the workpiece may be analyzed using any suitable apparatus, including, but not limited to, apparatuses of the inventive concept. In some embodiments, analyzing light reflected by the workpiece may comprise detecting light reflected by the workpiece with an array detector (e.g., an array detector as described above with respect to FIG. 1). Light reflected by the workpiece may be directly reflected to the array detector or may be redirected to the array detector by one or more intermediate reflectors (e.g., a light separator as described above with respect to FIGS. 1-2). Methods of the inventive concept may comprise detecting light reflected by the workpiece with a camera (e.g., a camera as described above with respect to FIG. 1). Light reflected by the workpiece may be directly reflected to the camera or may be redirected to the camera by one or more intermediate reflectors (e.g., a reflecting aperture as described above with respect to FIG. 1).

Methods of the inventive concept may comprise loading the workpiece W into a chamber (e.g., a chamber as described above with respect to FIG. 3), supplying one or more reaction gases into the chamber and processing the workpiece W (e.g., etching the workpiece to form one or more via holes V therein).

Methods of the inventive concept may comprise displaying one or more graphical representations (e.g., one or more intensity spectrums representing light reflected by the workpiece W), one or more images (e.g., one or more virtual images of the upper surface of the workpiece W) and/or one or more 3D representations (e.g., one or more 3D representations of structures in/on the workpiece W) on a display unit (see discussion above with respect to FIG. 3).

Accordingly, in some embodiments, the method comprises loading a workpiece W (e.g., a wafer) into a chamber 110 (by mounting it in/on a susceptor 120, for example), introducing one or more reaction gases into the chamber 110 (by way of a gas supplying unit 130, for example), processing the workpiece W (e.g., etching the workpiece), radiating a first polarized light Lp1 and a second polarized light Lp2 onto the workpiece W, separating light reflected by the workpiece W according to wavelength (using a light separator 270, for example) and analyzing the light reflected by the workpiece (using an array detector 290 and/or an analyzer 300, for example), wherein the first polarized light Lp1 oscillates in a first direction X, wherein the second polarized light Lp2 oscillates in a second direction Y different from the first direction X and wherein analyzing the light reflected by the workpiece W comprises comparing a first spectrum of reflected light that oscillates in the first direction X with a second spectrum of reflected light that oscillates in the second direction Y. In some such embodiments, the first direction X is perpendicular to the second direction Y.

Figure 5A:
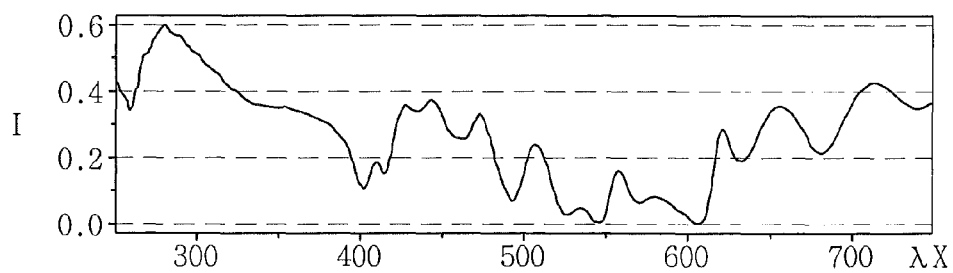
FIGS. 5A-5C are graphs illustrating intensity spectrums of polarized light reflected from a workpiece in accordance with an exemplary embodiment of the inventive concept (x axis=wavelength; y axis=intensity)
Figure 5B:
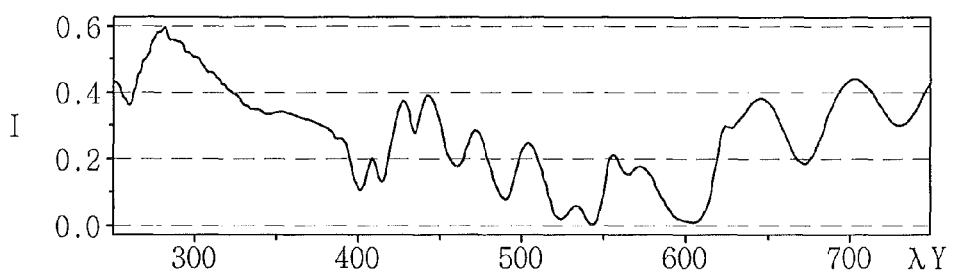

As indicated above, light reflected by a workpiece may be graphically represented as an intensity spectrum. For example, as shown in FIGS. 5A-5C, light reflected by a workpiece may be depicted in a graph wherein the horizontal axis represents the wavelengths of light reflected by the workpiece and the vertical axis represents the intensity of the light reflected by the workpiece.

Spectra representing light polarized in various one-dimensional directions may be depicted on a single graph and may be superimposed upon one another. Thus, a single graph may comprise a first spectrum representing reflected light polarized in a first direction, a second spectrum representing reflected light polarized in a second direction different from the first direction, a third spectrum representing reflected light polarized in a third direction different from the first and second directions, etc. Non-coincidence between the spectra may be indicative of asymmetry in the structure/pattern from which the light was reflected and may provide information as to the uniformity and/or stability of the underlying fabrication process(es).

Figure 5C:
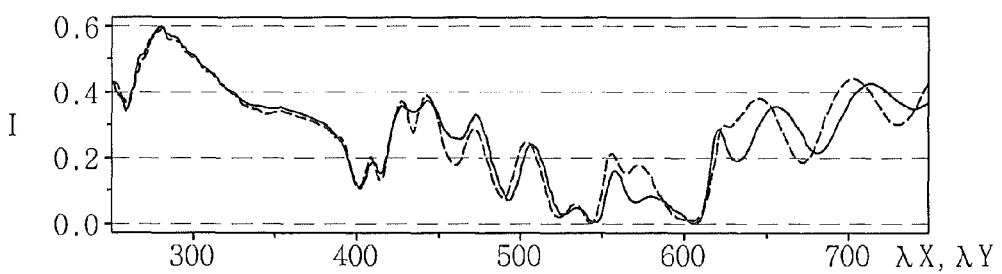

Accordingly, as shown in FIG. 5C, in some exemplary embodiments, light reflected by a workpiece is graphically represented as a first spectrum (solid line) representing reflected light polarized in a first direction and a second spectrum (dashed line) representing reflected light polarized in a second direction different from the first direction. Non-coincidence between the first and second spectra at particular wavelengths indicates that the profile of the structure/pattern in the inspection area IA is asymmetrical. For example, if the inspection area comprises a single via hole V, non-coincidence between the two spectra indicates that the profile of the via hole is asymmetrical (e.g., is elliptical in shape). If the inspection area comprises a plurality of via holes V, non-coincidence between the two spectra may provide information as to the uniformity and/or stability of the process(es) used to form the via holes.

As indicated above, graphical representations of the light reflected by workpiece may be generated repeatedly. When non-coincidence of the spectra generated during various cycles of a process is great and/or the variation in non-coincidence across cycles is great, the process may be deemed unstable. When non-coincidence of the spectra is low, the process may be deemed stable. For example, while a patterning process is performed, the processes of radiating a first polarized light Lp1 onto the workpiece W, sensing the first reflected light Lr1, radiating a second polarized light Lp2 onto the workpiece W and sensing the second reflected polarized light Lr2 may be repeatedly performed. The non-coincidence of the two spectra may be periodically monitored in real time.

Asymmetry in a structure/pattern in/on a workpiece may be calculated/estimated by comparing light reflected from the workpiece. For example, the asymmetry of a via hole may be calculated/estimated by comparing reflected light polarized in a first direction to reflected light polarized in a second direction different from the first direction. In some embodiments, asymmetry is calculated/estimated by 1) dividing the absolute value of the difference between the intensity of reflected light polarized in a second direction in each of the wavelengths and the intensity of reflected light polarized in a first direction in each of the wavelengths by one-half the absolute value of the sum of the intensity of reflected light polarized in the first direction in each of the wavelengths and the intensity of reflected light polarized in the second direction in each of the wavelengths, 2) adding the divided absolute values in the respective wavelengths and 3) dividing the added absolute values by the number of wavelengths, as shown in Equation 1 below $$A(\%) = \frac{1}{k}\sum_{n=1}^{k} \frac{|TX_n - TY_n|}{|TX_n + TY_n|/2} \times 100(\%) \qquad \text{Equation 1}$$

wherein n is a wavelength of sampled light, k is the number of wavelengths of the sampled light, TX is intensity of reflected light polarized in a first direction in a specific wavelength, TY is intensity of reflected light polarized in a second direction in the specific wavelength and A is asymmetry. When the asymmetry A is large, the shape of the via hole may be estimated as a shape having a large difference between shapes of the via hole according to polarization directions, for example, an ellipse-like shape. As the asymmetry A gets closer to zero, the shape of the via hole may be estimated as a symmetrical shape, for example, a shape close to a circle.

As indicated above, asymmetry may be calculated/estimated repeatedly. Asymmetries calculated/estimated during different cycles of a process may be used to construct a 3D representation of a structure/pattern in a workpiece. For example, as shown in FIGS. 6A-6B, asymmetries calculated/estimated during different cycles of an etching process may be used to construct a 3D representation of a via hole V in a workpiece W.

Figure 6A:
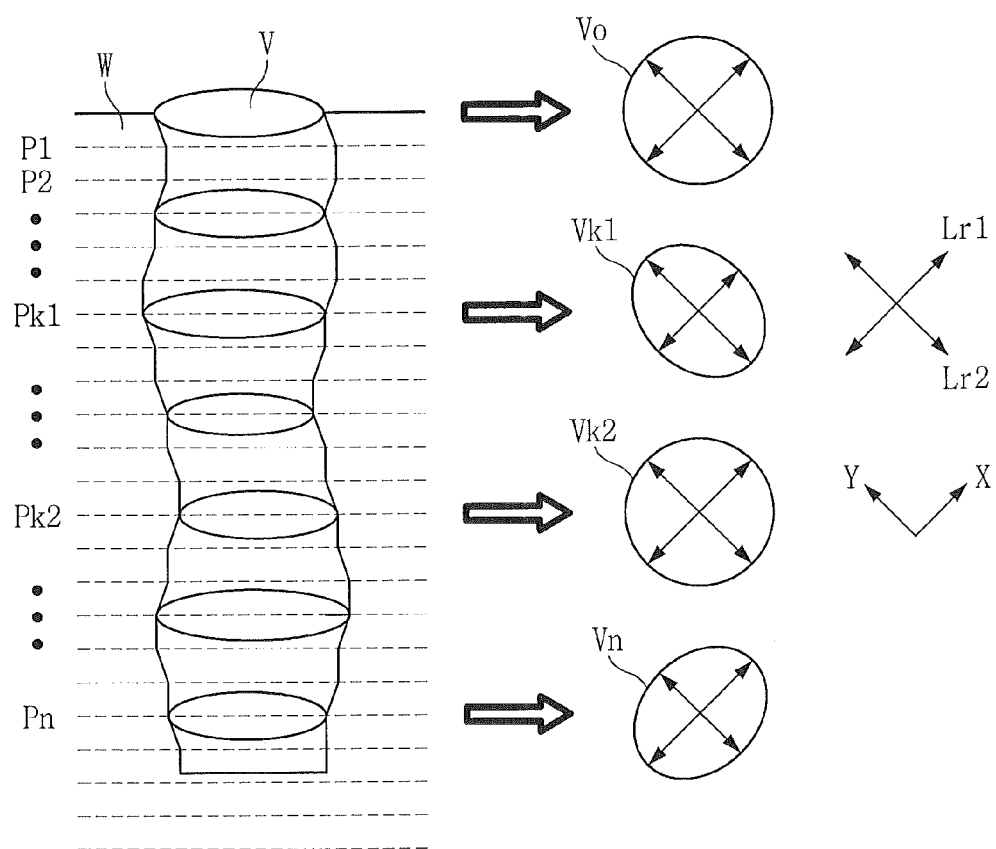
FIGS. 6A-6B are schematic illustrations of 3D profiles generated according to exemplary embodiments of the inventive concept.
Figure 6B:
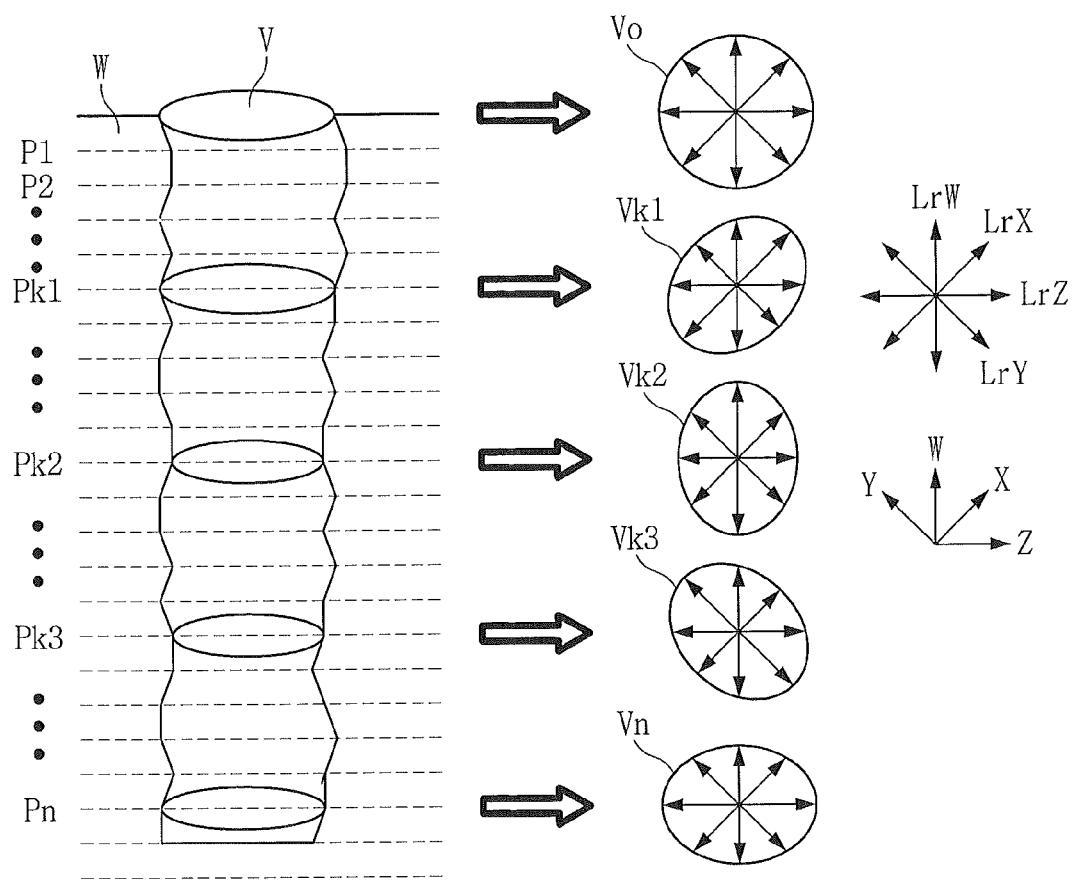

Accordingly, as shown in FIG. 6A, in some exemplary embodiments, a 3D profile of a via hole V depending on a depth of the via hole V is estimated. Arrows indicate an oscillation direction of the first reflected polarized light Lr1, and an oscillation direction of the second reflected polarized light Lr2. Specifically, when changes in asymmetries A1, . . . , Ak1, . . . , Ak2, . . . , An measured and calculated in a plurality of cycles P1, . . . , Pk1, . . . , Pk2, . . . , Pn are considered, the 3D profile of the via hole V changed depending on the depth of the via hole V, may be estimated. For example, the asymmetries are partially differentiated according to polarization directions (X and Y directions) of each of the reflected polarized lights Lr1 and Lr2 to calculate change rates of the asymmetries A1', . . . , Ak1', . . . , Ak2', . . . , An' and shapes (in the top view) of via holes V1, . . . , Vk1, . . . , Vk2, . . . , Vn in the cycles P1, . . . , Pk1, . . . , Pn, and the 3D profile of the entire via hole V may be estimated. For example, after the asymmetries A1, . . . , Ak1, . . . , Ak2, . . . , An per cycle P1, . . . , Pk1, . . . , Pk2, . . . , Pn are measured and calculated, change rates AX'Y and AXY' of the asymmetries in adjacent cycles P1 to Pn may be calculated using Equation 2 and/or Equation 3.

$$AX'Y = \frac{\partial}{\partial X} A \qquad \text{Equation 2}$$

$$AXY' = \frac{\partial}{\partial Y} A \qquad \text{Equation 3}$$

For example, when it is assumed that the shape in the top view of the via hole V is a circle, it can be seen that an elliptic shape in the first polarization direction (X direction) is intensified since the asymmetry Ax of the first polarization direction (X direction) is increased when the change rate AX'Y of the asymmetry in the first polarization direction (X direction) has a positive (+) value, and the shape of the via hole comes close to the circular shape since the asymmetry Ax of the first polarization direction (X direction) is reduced when the change rate AX'Y of the asymmetry has a negative (−) value. Similarly, it can be seen that an elliptic shape in the second polarization direction (Y direction) is intensified since the asymmetry Ay of the second polarization direction (Y direction) is increased when the change rate AXY' of the asymmetry in the second polarization direction (Y direction) has a positive (+) value, and the shape of the via hole comes close to the circular shape since the asymmetry Ay of the second polarization direction (Y direction) is reduced when the change rate AXY' of the asymmetry has a negative (−) value. When the processes are repeatedly performed during the patterning process, the change in the 3D profile of the via hole V according to the cycle, that is, the depth thereof, may be estimated. Therefore, the 3D profile of the via hole V may be estimated and imagined with reference to the change rates AX'Y and AXY' of the asymmetries measured per cycle P1 to Pn based on the shape in the top view of the via hole V on the surface of the wafer W.

As indicated above, the polarization direction and/or polarization azimuth may be diversified. For example, the polarization direction and/or the polarization azimuth may be diversified to $\pi/3$, $\pi/4$, $\pi/6$, $\pi/9$, or other various angles. Therefore, the asymmetries A measured and calculated according to various polarization directions or polarization azimuths and the change rates A' in the asymmetries, may provide a more detailed 3D profile of the via hole V and stability of the patterning process.

As shown in FIG. 6B, when the polarization direction or the polarization azimuth is changed in the cycle of $\pi/4$ such as $0$, $\pi/4$, $\pi/2$, $3\pi/4$, $\pi$, . . . , after a first asymmetry Aa of a first reflected polarized light LrX and a second reflected polarized light LrY in a pair of $0$ and $\pi/2$ and a change rate Aa' of the first asymmetry are measured and calculated, and a second asymmetry Ab of a third reflected polarized light LrW and a fourth reflected polarized light LrZ in a pair of $\pi/4$ and $3\pi/4$ and a change rate Ab' of the second asymmetry are measured and calculated, an integrated asymmetry At and change rate At' of the integrated asymmetry may be calculated by comparing the first asymmetry Aa and the second asymmetry Ab, and stability of the patterning process and the 3D profile of the via hole V may be estimated and imagined.

Alternatively, all polarization directions or all polarization azimuths may be compared. At this time, a low weight may be given to a polarization direction or polarization azimuth having relatively low change, and a high weight may be given to a polarization direction or polarization azimuth having relatively high change so that the asymmetries A and change rates A' of the asymmetries may be considered.

Arrows indicate oscillation directions of the first reflected polarized light LrX, second reflected polarized light LrY, third reflected polarized light LrW, and fourth reflected polarized light LrZ. The change rates A1', . . . , Ak1', . . . , Ak2', . . . , Ak3', . . . , An' of asymmetries may be calculated by partially differentiating the asymmetries A1, . . . , Ak1, . . . , Ak2, . . . , Ak3, . . . , An measured and calculated in a plurality of cycles P1, . . . , Pk1, . . . , Pk2, . . . , Pk3, . . . , Pn according to polarization directions of each of the reflected polarized lights LrX, LrY, LrW, and LrZ and shapes of via holes V1, . . . , Vk1, . . . , Vk2, . . . , Vk3, . . . , Vn in the cycles P1, . . . , Pk1, . . . , Pk2, . . . , Pk3, . . . , Pn, and a 3D profile of the entire via hole V may be estimated. For example, after the asymmetries A1, . . . , Ak1, . . . , Ak2, . . . , Ak3, . . . , An in cycles P1, . . . , Pk1, . . . , Pk2, . . . , Pk3, . . . , Pn are measured and calculated, change rates AX'YWZ, AXY'WZ, AXYW'Z, and AXYWZ' of the asymmetries in adjacent cycles P1 to Pn may be calculated using Equation 2 and/or Equation 3

However, even when the differentiation is not used, the 3D profile of the via hole V may be estimated. For example, when the intensity spectra of the reflected polarized lights LrX, LrY, LrW, and LrZ in each of the cycles P1, . . . , Pk1, . . . , Pk2, . . . , Pk3, . . . , Pn are compared, the planar shape of the via hole V changed depending on a depth thereof, may be estimated. Specifically, when the intensity spectra of the first reflected polarized lights Lr1 in the cycles P1, . . . , Pk1, . . . , Pk2, . . . , Pk3, . . . , Pn are compared and the intensity spectra of the second reflected polarized lights Lr2 in the cycles P1, . . . , Pk1, . . . , Pk2, . . . , Pk3, . . . , Pn are compared, the planar shape of the via hole V according to each of the polarization directions (X and Y directions) may be estimated and thus, change in an initial shape of the via hole on the surface of the wafer W may be estimated.

The semiconductor fabrication apparatus according to various embodiments of the inventive concept may monitor a process of processing a wafer in real time and estimate a 3D profile of a pattern. The monitoring method according to various embodiments of the inventive concept may provide stability of the process of processing a wafer and estimate a 3D profile of a pattern.

As will be appreciated by those skilled in the art, the inventive concept provides apparatuses and methods for monitoring semiconductor fabrication processes, for inspecting workpieces (e.g., wafers) during processing, for characterizing 3D structures (e.g., via holes) and patterns in a workpiece and/or for generating 3D profiles of structures/patterns in a workpiece. Indeed, as indicated above, apparatuses and methods of the inventive concept may be used to perform any of the aforementioned tasks in real time.

Moreover, as will be appreciated by those skilled in the art, apparatuses and methods of the inventive concept may increase the efficiency with which semiconductor devices are formed.

The foregoing is illustrative of embodiments and is not to be construed as limiting thereof. Although a few embodiments have been described, those skilled in the art will readily appreciate that many modifications are possible without materially departing from the novel teachings and advantages of the inventive concept. Accordingly, all such modifications are intended to be included within the scope of this inventive concept as defined in the claims. In the claims, means-plus-function clauses are intended to cover the structures described herein as performing the recited function, and not only structural equivalents but also equivalent structures.

What is claimed is:

1. An apparatus, comprising:
a polarizing spectroscopic reflector module, said module comprising:
a light source configured to generate light;
a beam splitter configured to reflect light generated by the light source toward a workpiece;
an objective polarizer configured to polarize light reflected by the beam splitter toward the workpiece and to allow light reflected by the workpiece to reversely pass therethrough, wherein the light reversely passes through the objective polarizer toward the beam splitter, wherein the objective polarizer is configured to rotate around an optical axis and polarize the light reflected by the beam splitter such that the light oscillates in a plurality of one-dimensional directions;

a blaze grating configured to reflect light that is reflected by the workpiece and reversely passed through the objective polarizer and the beam splitter; and an array detector configured to sense light reflected by the blaze grating.

2. The apparatus of claim 1, wherein the light generated by the light source is polychromatic ultraviolet light.

3. The apparatus of claim 1, wherein an optical axis of light reflected by the beam splitter toward the workpiece is perpendicular to a surface of the workpiece.

4. The apparatus of claim 1, wherein the blaze grating comprises a plurality of sawtooth-shaped reflecting surfaces that divide, according to wavelength, light reflected by the surface of the workpiece and passed through the objective polarizer.

5. The apparatus of claim 1, further comprising a chamber, wherein the polarizing spectroscopic reflector module is at least partially disposed in a top portion of said chamber.

6. The apparatus of claim 5, further comprising a gas distributor configured to introduce one or more reaction gases into the chamber.

7. The apparatus of claim 1, further comprising a reflecting aperture configured to reflect a portion of the light reflected by the workpiece and passed through the objective polarizer.

8. The apparatus of claim 7, further comprising a camera configured to sense light reflected by the reflecting aperture.

9. The apparatus of claim 1, further comprising an analyzer configured to analyze light sensed by the array detector.

10. The apparatus of claim 9, further comprising a display unit configured to display a graphical representation of the intensities of light reflected by the workpiece as a function of wavelength.

11. The apparatus of claim 6, wherein the gas distributor includes a space configured to mix reaction gases, and a baffle plate configured to supply the reaction gases to the inside of the chamber, and wherein the polarizing spectroscopic reflector module vertically passes through a central portion of the baffle plate.

12. An apparatus comprising:
a chamber; and
a polarizing spectroscopic reflector module configured to radiate polarized light onto a workpiece and to sense light reflected by the workpiece,
wherein said polarizing spectroscopic reflector module comprises:
a light source configured to generate light;
a beam splitter configured to reflect light generated by the light source;
an objective polarizer configured to polarize light reflected by the beam splitter toward the workpiece, wherein the light reflected by the workpiece reversely passes through the objective polarizer toward the beam splitter, wherein the objective polarizer is configured to rotate around an axis that is perpendicular to a surface of the workpiece and polarize the light reflected by the beam splitter such that the light oscillates in a plurality of one-dimensional directions;

a blaze grating configured to reflect light that is reflected by the workpiece and reversely passed through the objective polarizer and the beam splitter; and an array detector configured to sense light reflected by the blaze grating.

13. The apparatus of claim 12, further comprising a gas distributor configured to mix reaction gases and to introduce the mixed reaction gases into the chamber.

14. The apparatus of claim 12, wherein the polarizing spectroscopic reflector module further comprises:
a reflecting aperture configured to reflect a portion of the light reflected by the workpiece; and
a camera configured to sense light reflected by the reflecting aperture.

15. The apparatus of claim 13, wherein the gas distributor includes a space configured to mix reaction gases, and a baffle plate configured to supply the reaction gases to the inside of the chamber, and wherein the polarizing spectroscopic reflector module vertically passes through a central portion of the baffle plate.

16. An apparatus, comprising:
a chamber having a susceptor configured to place a workpiece in a lower portion of an inside thereof, wherein the chamber comprises a gas distributor disposed in an upper portion of the inside thereof, wherein the gas distributor comprises a space configured to mix reaction gases, and a baffle plate configured to supply the reaction gases to the inside of the chamber; and
a polarizing spectroscopic reflector module disposed in a center of a top of the chamber and that vertically passes through a central portion of the baffle plate, wherein the polarizing spectroscopic reflector module includes:
a light source configured to generate light;
a beam splitter configured to receive the light generated from the light source and reflect a portion of the received light;
an objective polarizer configured to polarize the portion of the light reflected by the beam splitter and radiate the polarized light to the workpiece on the susceptor, wherein reflected polarized light reflected from the workpiece reversely passes through the objective polarizer, and the reflected polarized light reversely passed through the objective polarizer partially passes through the beam splitter;
a reflecting aperture configured to partially pass the reflected polarized light passing through the beam splitter;
a blaze grating configured to reflect the reflected polarized light partially passing through the reflecting aperture; and
an array detector configured to sense the reflected polarized light divided and reflected by the blaze grating.

17. The apparatus of claim 16, wherein an optical axis of the polarized light radiated to a surface of the susceptor from the objective polarizer is perpendicular to the surface of the susceptor.

18. The apparatus of claim 16, wherein the beam splitter and the reflecting aperture reflect a portion of the received light and pass another portion of the received light.

* * * * *